(12) United States Patent
Willey et al.

(10) Patent No.: US 8,883,710 B2
(45) Date of Patent: *Nov. 11, 2014

(54) COMPOSITIONS AND METHODS INCORPORATING PHOTOCATALYSTS

(75) Inventors: Alan David Willey, Cincinnati, OH (US); Ellen Schmidt Baker, Cincinnati, OH (US); William Richard Mueller, Cincinnati, OH (US); Ioannis Constantine Constantinides, Wyoming, OH (US)

(73) Assignee: The Procter & Gamble Company, Cincinnati, OH (US)

(*) Notice: Subject to any disclaimer, the term of this patent is extended or adjusted under 35 U.S.C. 154(b) by 794 days.

This patent is subject to a terminal disclaimer.

(21) Appl. No.: 12/768,037

(22) Filed: Apr. 27, 2010

(65) Prior Publication Data

US 2010/0247800 A1  Sep. 30, 2010

Related U.S. Application Data

(63) Continuation-in-part of application No. 12/433,958, filed on May 1, 2009.

(60) Provisional application No. 61/260,900, filed on Nov. 13, 2009, provisional application No. 61/261,032, filed on Nov. 13, 2009, provisional application No. 61/053,831, filed on May 16, 2008.

(51) Int. Cl.

| | | |
|---|---|---|
| C11D 17/00 | (2006.01) | |
| A61K 8/893 | (2006.01) | |
| C11D 3/40 | (2006.01) | |
| A61Q 19/00 | (2006.01) | |
| A61Q 5/04 | (2006.01) | |
| A61Q 5/10 | (2006.01) | |
| A61Q 5/00 | (2006.01) | |
| A61Q 5/12 | (2006.01) | |
| A61Q 5/06 | (2006.01) | |

(52) U.S. Cl.
CPC .............. *A61K 8/893* (2013.01); *A61K 2800/81* (2013.01); *A61Q 5/04* (2013.01); *A61Q 5/10* (2013.01); *C11D 3/40* (2013.01); *A61Q 19/00* (2013.01); *A61Q 5/00* (2013.01); *A61Q 5/12* (2013.01); *A61Q 5/06* (2013.01)
USPC ............ 510/424; 510/426; 510/428; 510/499

(58) Field of Classification Search
None
See application file for complete search history.

(56) References Cited

U.S. PATENT DOCUMENTS

| | | |
|---|---|---|
| 5,906,610 A | 5/1999 | Mehl |
| 6,283,956 B1 | 9/2001 | McDaniel |

(Continued)

FOREIGN PATENT DOCUMENTS

| | | |
|---|---|---|
| CN | 1980969 A | 6/2007 |
| JP | A-2006-189819 | 4/2006 |

(Continued)

OTHER PUBLICATIONS

International Search Report dated Jul. 9, 2010 containing 15 pages.

*Primary Examiner* — Necholus Ogden, Jr.
(74) *Attorney, Agent, or Firm* — Jason J Camp; Kim W Zerby

(57) ABSTRACT

The present invention includes compositions comprising an active material having groups capable of covalent attachment to a substrate in the presence of an acid or a base, a photocatalyst capable of generating an acid or a base upon exposure to light, and a vehicle. Also included herein is a method for treating a substrate with these compositions. The method includes the steps of applying at least one active material having functional groups to the substrate, applying a photocatalyst to the substrate, and exposing the photocatalyst and the at least one active material to light for forming covalent attachments between the functional groups and constituent groups on the substrate. The compositions and methods described herein are useful in consumer care and personal care product applications.

15 Claims, 7 Drawing Sheets

(56) References Cited

U.S. PATENT DOCUMENTS

| | | |
|---|---|---|
| 2003/0091602 A1 | 5/2003 | Witteler |
| 2003/0113279 A1 | 6/2003 | Vic |
| 2003/0187088 A1 | 10/2003 | Yoshikawa et al. |
| 2003/0215649 A1 | 11/2003 | Jelle |
| 2004/0043046 A1 | 3/2004 | Vic |
| 2005/0112154 A1 | 5/2005 | Giroud |
| 2005/0136538 A1* | 6/2005 | Pathak et al. .......... 435/395 |
| 2005/0186151 A1 | 8/2005 | Giroud |
| 2005/0208005 A1 | 9/2005 | Giroud |
| 2009/0285768 A1* | 11/2009 | Baker et al. ............ 424/59 |
| 2010/0063221 A1 | 3/2010 | Manabe et al. |
| 2010/0247800 A1* | 9/2010 | Willey et al. .......... 427/553 |

FOREIGN PATENT DOCUMENTS

| | | |
|---|---|---|
| JP | A-2007-065129 | 3/2007 |
| WO | WO 01/06829 A2 | 2/2001 |
| WO | WO-2005121200 A1 | 12/2005 |
| WO | WO 2007/127065 | 11/2007 |
| WO | WO-2008157604 A1 | 12/2008 |

* cited by examiner

COMPOSITIONS AND METHODS INCORPORATING PHOTOCATALYSTS

CROSS REFERENCE TO RELATED APPLICATION

This application seeks priority to U.S. Ser. No. 12/433,958 filed May 1, 2009 that has priority to U.S. Application 61/053,831(11060P), filed May 16, 2008; U.S. Application 61/260,900, filed Nov. 13, 2009 (case 11492P); and U.S. Application 61/261,032 (case 11493P), filed Nov. 13, 2009.

FIELD OF THE INVENTION

A composition for and method of covalent modification of surface properties of a substrate, comprising a silicone polymer, copolymer and mixtures thereof and an active material having functional groups capable of covalent attachment to a substrate in the presence of an acid or a base, a photocatalyst capable of generating an acid or a base upon exposure to light, and a vehicle.

BACKGROUND OF THE INVENTION

Materials may be characterized in terms of bulk properties and surface properties. The overall properties of a material are controlled in significant part by the surface properties and the bulk properties of the material. The surface properties of a material are largely controlled by the surface chemistry and surface structure of the material. The bulk properties of a material are largely controlled by the bulk chemistry and bulk structure of the material. It is sometimes desirable to modify the surface chemistry and/or surface structure of a material in order to produce certain surface properties. In addition, it is sometimes desirable to modify the bulk chemistry and/or bulk structure of a material in order to produce certain bulk properties.

Substrates including hair and skin are of interest in terms of surface and/or bulk modification. Substrates are repeatedly exposed to mechanical washings, chemical treatments and environmental conditions which are among the many factors that may result in the loss of the substrates desirable properties such as natural and synthetically created shine, luster and texture. Moreover, environmental factors may add to these effects and substantially contribute to weathered or damaged substrates. Acute damage to the surface of substrates including hair and skin may build over time, resulting in chronic damage.

Accordingly, there exists a need for compositions and methods to compensate for things such as F-layer and stratum corneum loss from hair fibers and skin, respectively, that provides a durable conditioning and protective benefit. Covalent modification of the surface properties of damaged substrates materials is one example of such an approach. There is also a need to protect, repair, and/or strengthen these materials. Modification of the surface of a material by locally forming an active material on the material surface by reacting one or more active components to create covalent bonds between the one or more active components and modification the bulk of a material by forming active material in a similar manner within the bulk of the material are promising approaches.

SUMMARY OF THE INVENTION

A composition comprising: an active material having one or more functional groups capable of covalent attachment in the presence of an acid or a base to one or more complementary functional groups; a photocatalyst capable of generating an acid or a base upon exposure to light; and a vehicle for dispersing or dissolving the active material and photocatalyst for application of the composition to a substrate; wherein the active material is selected from the group consisting of silicone polymers, copolymers, and mixtures thereof and at least one organic functional group.

A method for treating a substrate comprising applying to the substrate the composition previously described and exposing the composition-treated substrate to ambient light. Alternatively this method can be carried out in multiple steps wherein the method comprises the steps of applying at least one active material to the substrate, the active material having one or more functional groups, and the substrate having one or more complementary functional groups; applying to the substrate at least one photocatalyst capable of generating an acid or base on exposure to light; and exposing the photocatalyst and the at least one active material to light. Whichever method is used, exposure to light results in the forming covalent attachments between the one or more functional groups of the at least one active material and the substrate.

BRIEF DESCRIPTION OF THE DRAWINGS

Various embodiments described herein may be understood by reference to the following description, taken with the accompanying drawings as follows.

DETAILED DESCRIPTION OF THE INVENTION

Figure 1:
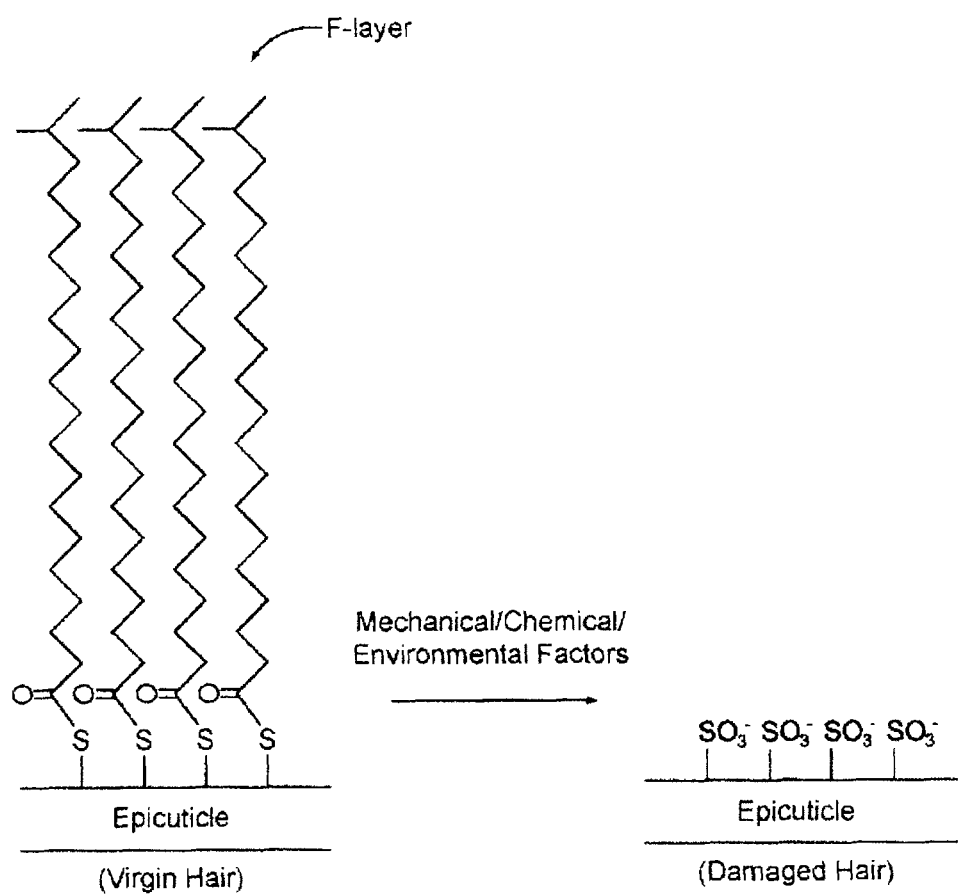
FIG. 1 is a schematic diagram that illustrates damage to the FCSM of a fiber comprising a covalently bound to 18-MEA by way of thioester bonds.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

As used herein, the term "functional group" means an atom or group of associated atoms that, at least in part, defines the structure and determines the properties of a particular family of chemical compounds. A functional group may be a region on or in a molecule or material that is a site of specific chemical reactivity compared to other regions of the molecule or material. Functional groups generally have characteristic properties and may control, in part, the reactivity of a molecule as a whole. Functional groups include, but are not limited to, hydroxyl groups, thiol groups, carbonyl groups, carboxyl groups, sulfonate groups, sulfide groups, ether groups, halogen atoms, amino groups, cyano groups, nitro groups, and the like. Compounds that are generally classified (structurally and/or functionally) according to functional groups include, but are not limited to, alkanes, alkenes, alkynes, aromatic compounds, halides, alcohols, ethers, esters, amines, imines, imides, carboxylic acids, amides, acid halides, acid anhydrides, nitriles, ketones, aldehydes, carbonates, peroxides, hydroperoxides, carbohydrates, acetals, epoxides, sulfonic acids, sulfonate esters, sulfides, sulfoxides, thioethers, thiocyanates, disulfides, phosphonic acids, phosphate esters, phosphines, azides, azo compounds, nitro compounds, nitrates, nitriles, nitrites, nitroso compounds, thiols, cyanates, and isocyanates, for example.

The terms "active material", "active component", "active compound", and combinations and modifications of these terms, as used herein means substances to be applied to a substrate to modify the surface and/or bulk properties of the substrate material. These terms may be used interchangeably. Substrate surface properties may include, for example, surface hydrophobicity/hydrophilicity, oleophobicity/oleophilicity, color, optical properties, absorptivity, adsorptivity, bonding capability, brightness, dullness, frictional resistance, stain resistance, surface texture, odor, washability, wettability, elasticity, plasticity, and rigidity. Substrate bulk properties may include, for example, tensile strength, rigidity, absorptivity, elasticity, plasticity, and biological activity.

Active materials may include compounds having one or more functional groups capable of covalent attachment in the presence of an acid or a base to one or more complementary functional groups present at the surface or in the bulk of a substrate. Active materials may also include compounds capable of forming covalent bonds between molecules in the presence of an acid or a base, for example, monomers capable of acid or base catalyzed polymerization and, or copolymerization. A "cosmetically active material" is an active material suitable for use in a personal care product without undue toxicity, incompatibility, instability, allergic response, and the like.

The term "monomer" as used herein means a compound that may be covalently bonded to other monomers (that may have the same or different chemical structures) to form a polymer and, or copolymer. The term "polymer and "copolymer as used herein means a compound comprising a plurality of monomers. Accordingly, as used herein the term polymer and, or copolymer includes dimers, trimers, oligomers, and the like.

As used herein, the terms "modify", "modification", "functionalize" or "functionalization", with regard to a substrate, refers to (1) covalently attaching an active component to the substrate surface, (2) covalently attaching an active component to the substrate in the bulk of the substrate material, (3) forming covalent bonds between two or more active components (which may be the same or different chemical moieties) where the resultant secondary active material localizes to the substrate surface, and/or (4) forming covalent bonds between two or more active components (which may be the same or different chemical moieties) where the actives components are present within the bulk of the substrate.

The term "consumer care product" as used herein means a product such as, for example, soft surface cleaners, hard surface cleaners, glass cleaners, ceramic tile cleaners, toilet bowl cleaners, wood cleaners, multi-surface cleaners, surface disinfectants, dishwashing compositions, laundry detergents, fabric conditioners, fabric dyes, surface protectants, surface disinfectants, motor vehicle surface treatments, and other like consumer products. Consumer care products includes form such as liquids, gels, suspensions, powders, and the like. Consumer care products may also be for household or home care use as well as for professional, commercial and/or industrial use.

Consumer care products include "personal care product" such as, for example, lipsticks, mascaras, rouge, foundations, blush, eyeliners, lip liners, lip gloss, nail polish, nail conditioner other cosmetics; personal care products including facial powders, body powders; hair treatment products including mousse, hair spray, styling gels, shampoo, hair conditioner (leave-in or rinse-out), cream rinse, hair dye, hair coloring product, hair shine product, hair serum, hair anti-frizz product, hair split-end repair product, permanent waving solution, antidandruff formulation; bath gels, shower gels, body washes, facial cleaners, skin care products including sunscreen and sun block lotions, lip balm, skin conditioners, cold creams, moisturizers, body spray, soap, body scrub, exfoliants, astringent, scrubbing lotion, depilatory, antiperspirant composition, deodorant, shaving product, pre-shaving product, after shaving product, toothpaste, mouthwash, or oral care strips.

The term "cleaner" as used herein includes compositions for cleaning substrates including, but not limited to hair or skin, including scalp, face, and body. Accordingly, the term "shampoo" includes, but is not limited to, the conventional understanding of a hair shampoo, a body wash, a face wash, or other surface washing composition, for example. In addition, the term "shampoo" includes compositions for use on humans and/or animals.

The term "conditioner" as used herein means a composition for treating substrates comprising fibrous material including fabrics, hair, and skin that includes scalp, face, and body, in order to provide protection to the substrate from mechanical, chemical, and/or environmental factors that contribute to damage and, or weathering, and/or to alleviate the characteristics of such damage. In this context, the term "conditioner" includes, but is not limited to, the conventional understanding of a fabric and hair conditioner (leave-on and/or rinse-out), a skin lotion, or a facial moisturizer, for example.

One object of the compositions and methods described herein is to provide for the modification of the surface and/or bulk properties of a substrate by covalently attaching an active material to the surface of the substrate. Another object of the compositions and methods described herein to provide for the modification of the surface and/or bulk properties of a substrate by treating the substrate with active compounds capable of reacting with each other to form covalent bonds between two or more molecules of the active compounds thereby forming a secondary active material. It is still another object of the compositions and methods described herein to provide for the functionalization of the surface of a substrate by covalently attaching active material to the surface of the substrate. In order to achieve effective treatment, it is occasionally desirable to initially attach onto a substrate a active material that contains multiple similar functional groups in its molecule, followed by another step of attaching another active material/benefit agent by reacting with the initially attached active material. This is especially useful if the substrate contains only limited density of functional groups that are able to react with a active material/benefit agent towards a chemical bond. For Example, initial attachment of malic acid (2-hydroxy-1,4-dibutanoic acid) onto a substrate increases the reactivity of the substrate by a factor of two towards subsequent attachment of an active. It is yet another object of the compositions and methods described herein to provide for such modification/functionalization in a manner that is readily amenable to health and safety regulations, and which may be readily implemented in a personal care product and/or a consumer care product space.

The various embodiments relate, in general, to compositions and methods for treating a substrate. As used herein, the term "substrate" means any material for which it is useful to treat the surface and/or bulk of that material with the compositions and methods described herein. The terms "substrate" and "material" may be used interchangeably in the context of substances to be modified by the compositions and methods described herein. In addition to the physiological materials, including, but not limited to, physiological materials such as, for example, hair, skin, nails, gums, and teeth. Substrate may also mean non-physiological materials such as, for example, fabric, paper, wood, plastic, glass, tile, stone, concrete, brick, other ceramics, coated or painted metal surfaces, coated glass, polymeric films, and composites or combinations thereof. Substrates may also include surfaces that have been previously modified such as, for example, coated surfaces (e.g., varnished or painted) or laminated surfaces. The terms "substrate" and "material" may be used interchangeably in the context of substances to be modified by the compositions and methods described herein. In various embodiments, the compositions described herein include an active component that can modify a substrate in the presence of an acid or a base, a photocatalyst capable of generating an acid or a base upon exposure to light, and a suitable vehicle, which may optionally be a physiological acceptable vehicle. In various embodiments, the compositions described herein may also include one or more optional components, including surfactants, emulsifiers, oxidants, reductants, pH regulators, emollients, humectants, proteins, peptides, amino acids, additive polymer or copolymers, glossers, essential oils and/or fatty acids, lubricants, sequestrants/chelators, antistatic agents, rheology modifiers, feel agents, fillers, preservatives, perfumes, other functional components, or combinations thereof.

In various embodiments, the methods described herein include treating a substrate by forming one or more covalent bonds between an active material and/or the substrate, where the covalent bond is formed in the presence of an acid or base generated by a photocatalyst upon exposure to light. In various embodiments, the methods described herein include treating a substrate by forming one or more covalent bonds between two or more active component's molecules, where the covalent bond is formed in the presence of an acid or base generated by a photocatalyst upon exposure to light and the active material localizes to the surface and/or bulk of the substrate. As used herein, the term "molecule" means a sufficiently stable group of at least two atoms in a definite arrangement held together by chemical bonds. Accordingly, the term molecule includes, but is not limited to, neutral molecular compounds, polyatomic ions, radical species, biomolecules, monomers, dimers, trimers, oligomers, polymer or copolymers, and the like. In various embodiments, the methods described herein include treating a substrate by preparing and covalently bonding a active material to the substrate, or forming covalent bonds between active materials on the substrate surface or in the substrate bulk, in situ, by providing a substrate, providing one or more reagents, providing a photocatalyst, and exposing the photocatalyst to light in the presence of the substrate and the one or more reagents, where the photocatalyst generates an acid or a base, the acid or the base catalyzes reaction between the one or more reagents and/or reaction between the one or more reagents and the substrate, and where the reaction(s) forms covalent bonds. In various embodiments, the methods described herein include providing a system including a substrate, an active material that can modify a substrate in the presence of an acid or a base, and a photocatalyst capable of generating an acid or a base upon exposure to light, and exposing the system to light.

Generally, covalent attachment of active materials on substrates such as hair and skin, for example, often proves difficult to achieve. This is especially true in the presence of water, which may rapidly degrade reactive moieties before substrate functionalization occurs. Moreover, aqueous media are known to chemically facilitate hydrolysis and oxidation reactions that may compete against covalent attachment of active materials to substrates. This may pose particular problems, for example, in consumer care products where water is often used as a physiologically acceptable vehicle. Consumer care products also often use water in a variety of capacities, most notably as a solvent.

In addition, substrates such as, for example, hair, skin, fabric, glass and ceramic may not contain particularly reactive chemical functional groups on the surface that would readily react with active components to form covalent bonds. This relatively low substrate surface reactivity may result in a reaction system that is outside the practical time frame of an apply-and-rinse environment (e.g., shampooing and conditioning hair, washing skin, laundering fabrics, or cleaning hard surfaces). Furthermore, strict regulatory requirements concerning product safety and environmental protection increase the challenge of providing compositions and methods for treating a substrate such as, for example, hair, skin, fabric, glass or ceramic, through covalent attachment of active components.

However, the various embodiments of the compositions and methods described herein are directed toward a photocatalyst technology that allows the use of light to promote a reaction such as, for example, the covalent attachment of an active component to a substrate or formation of covalent bonds between two or more active components in situ on the surface or in the bulk of a substrate material. The various embodiments may be used, for example, to promote the covalent attachment of long-chain alkyl groups to damaged hydrophilic hair and/or skin in order to replenish and/or fortify the normally hydrophobic character of these substrates. In addition, the various embodiments may be used, for example, to promote the covalent attachment of active materials to fabrics or hard surfaces. Furthermore, the various embodiments may be used, for example, to locally polymer or copolymerize monomers on the surface and/or in the bulk of substrate materials in order to modify the surface and/or bulk properties of a material.

In various embodiments, covalent attachment may yield a variety of substantial benefits. For example, fibers such as hair or fabric may experience conditioning benefits including, among others, improved feel, lower friction, ease of manipulation such as weaving, braiding combing/brushing, reduced dryness, increased smoothness, decreased frizziness, increased shine, decreased levels of static, and improved protection against damage due to other mechanical, chemical and environmental factors. For physiological substrates such as skin conditioning benefits may include, among others, decreased dryness, decreased redness, decreased itchiness, decreased flaking, and improved texture and smoothness. At least some of these benefits may be imparted by increased or targeted deposition of actives resulting from the surface modification via covalent attachment. For non-physiological substrates that are hard surfaces such as glass or ceramic tile, benefits may include reduced water spotting, increased shine or luster and easier subsequent cleaning. The benefits imparted by the compositions and methods described herein are potentially more durable because a non-labile covalent bond is employed, which is generally stronger and more stable relative to the absorption, adsorption, hydrogen bonding, ionic bonding, other electrostatic interactions, and/or other transient non-covalent associations employed in prior conditioners to deposit or apply active components onto hair and/or skin. This may substantially reduce the frequency of application and reapplication encountered with prior conditioners.

Various embodiments of the compositions and methods described herein provide for the covalent attachment of active materials to substrates, which may be described as an approach toward repairing and/or fortifying the hair F-layer or skin stratum corneum for example. In the context of fibers including hair, and not to be bound or otherwise limited by theory, the F-layer of virgin hair may be stripped from the hair fiber by processes mediated by various mechanical, chemical, and/or environmental factors as illustrated in FIG. 1. These processes may include, for example, the oxidative and hydrolytic reactions commonly encountered during permanent hair coloring and permanent waving processes.

FIG. 1 is a schematic diagram that illustrates the FCSM of a hair fiber comprising a keratinous epicuticle portion covalently bound to 18-MEA by way of thioester bonds between the carboxyl group on the 18-MEA and the thiol group on cysteine residues in the keratin protein in the epicuticle. Hydrolytic and/or oxidative processes (for example, due to the combinations of hydrogen peroxide, ammonia and high pH commonly encountered during permanent hair coloring and permanent waving processes), as well as other mechanical, chemical, and environmental factors, may remove at least a portion of the F-layer by cleaving the cysteine-lipid thioester bond, leaving exposed epicuticle comprising sulfonate groups on the cysteine residues.

The anionic sulfonate groups on the cysteine residues at the surface of the epicuticle render the surface of any damaged hair fibers hydrophilic, which may result in the undesirable properties of damaged hair. Moreover, it has been observed that the more hydrophilic (and consequently the more damaged) the hair fibers, the lower the deposition of prior hydrophobic conditioning actives (such as, for example, dimethylsiloxanes, fatty alcohols and acids, and quaternary amines) by non-covalent interactions and associations. Accordingly, the compositions and methods described herein provide an attractive approach for treating such damaged substrates.

Figure 2:
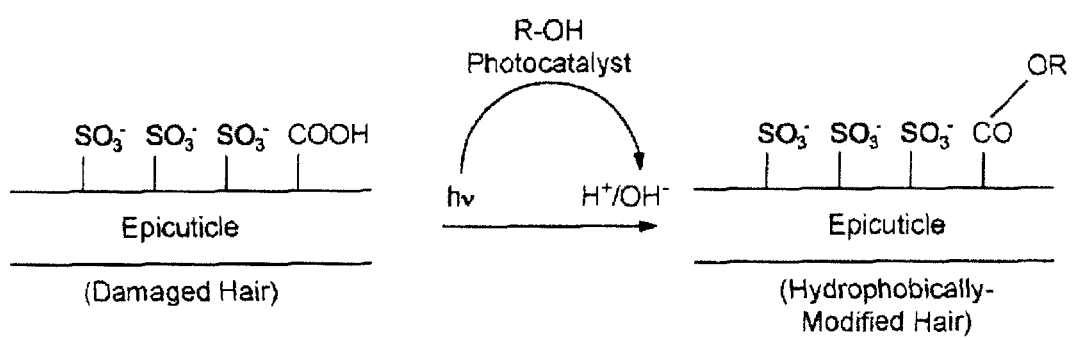
FIG. 2 is a schematic diagram that illustrates one non-limiting embodiment of the compositions and methods described herein for treating substrates including fibers with an active component and a photocatalyst.

FIG. 2 schematically illustrates one non-limiting embodiment of the compositions and methods described herein for treating substrates. A composition comprising an active component having a hydroxyl group (R—OH) and a photocatalyst capable of generating an acid or a base upon exposure to light is provided in the presence of a substrate comprising surface sulfonate and carboxyl groups. The photocatalyst is exposed to light, which causes the photocatalyst to form an acid or a base. The acid or base catalyzes the formation of a covalent ester bond between the hydroxyl group on the active material and the carboxyl group on the substrate.

Figure 3:
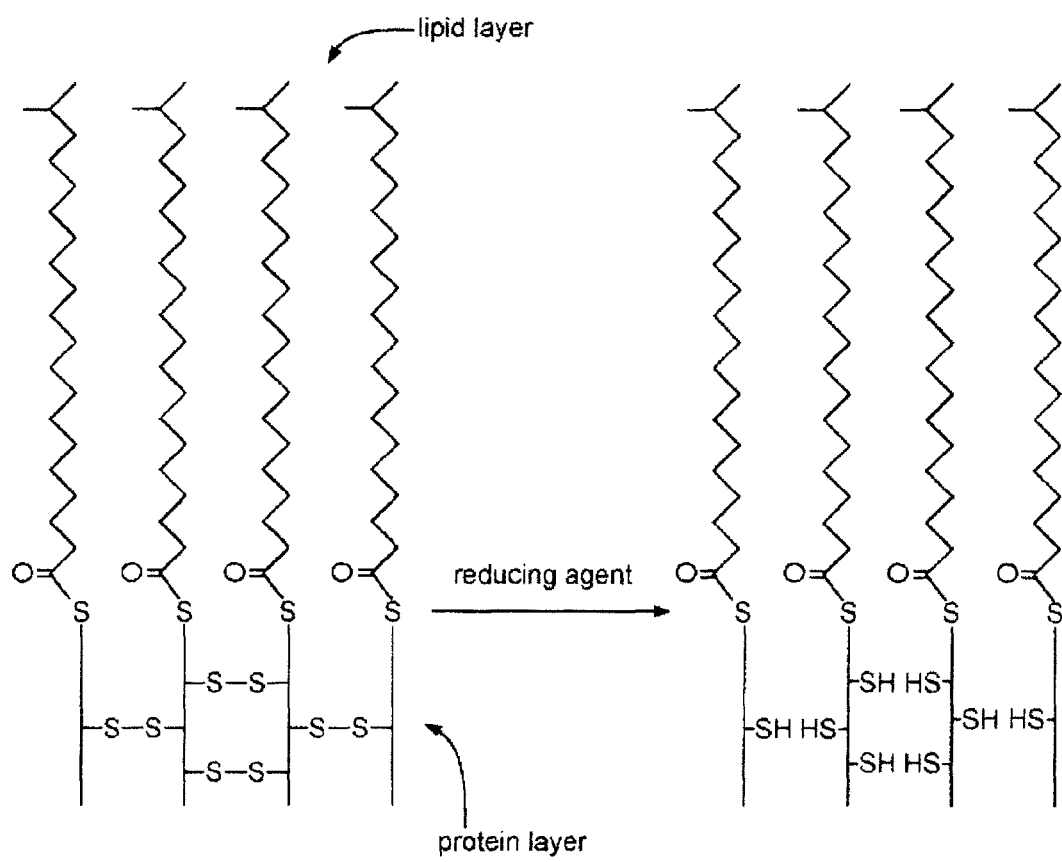
FIGS. 3 and 3A are schematic diagrams that illustrate one non-limiting embodiment of the compositions and methods described herein for treating physiological substrates such as fibers with an active component and a photocatalyst.
Figure 3A:
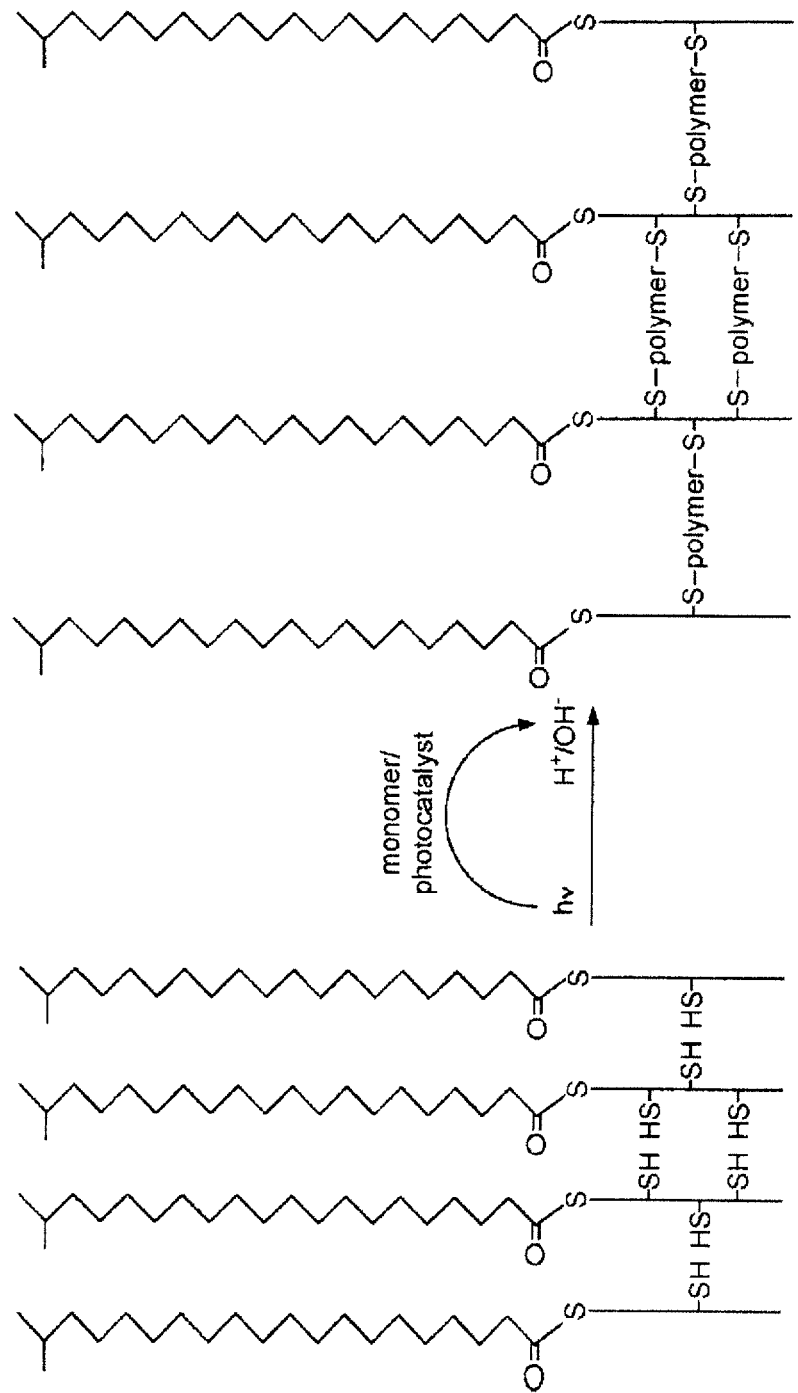

FIG. 3 and FIG. 3A, viewed together, schematically illustrate one non-limiting embodiment of the compositions and methods described herein for treating substrates. A portion of a hair fiber comprising a lipid layer (F-layer) and a protein layer (epicuticle) is shown. The protein layer comprises structural proteins such as, for example, keratin having disulfide bonds between cysteine residues. The hair may be treated with a reducing agent to break the disulfide bonds and form respective thiol groups. The hair may be further treated with an active component comprising one or more compounds capable of reaction to form covalent bonds between the one or more active component compounds and/or between the one or more active component compounds and the thiol groups. The hair fiber is also treated with a photocatalyst. The one or more active components and the photocatalyst penetrate the surface of the hair fiber substrate. The hair fiber substrate treated with the one or more active components and photocatalyst is exposed to light of suitable wavelength to activate the photocatalyst and catalyze reaction between the one or more active components within the hair fiber substrate and the thiol groups.

In various embodiments, the active materials may be one or more monomers capable of polymerizing or copolymerizing in the presence of acid or base. Fibers are treated with a composition comprising photocatalyst and active material monomers that at least partially penetrate the fiber. Upon exposure to light, the photocatalyst is activated thereby generating acid or base, which catalyzes the active material monomers to polymerize or copolymerize the monomers, thereby forming a active material polymer or copolymer in situ, which may optionally attach to the fiber by way of covalent bonds formed between the thiol groups and the polymer or copolymer.

In other embodiments (not shown), these active material polymers or copolymers do not covalently attach to the fiber. For example, the polymer or copolymer formed in situ may be physically immobilized on the surface of the hair fiber or within pores in the hair fiber. The polymer or copolymer formed in situ may also be associated with the hair fiber by a physical and/or chemical interaction such as, for example, adsorption, absorption, electrostatic interaction, frictional interaction, steric interaction, and/or size exclusion effects with the surface and/or bulk of the substrate.

In various embodiments, the active material monomers may be styrene or a styrene derivative such as, for example, α-methyl styrene. The monomer may also comprise mixtures of different monomers such that the in situ polymer or copolymerization (on the surface and/or in the bulk of the substrate) produces copolymer or copolymer.

Figure 4:
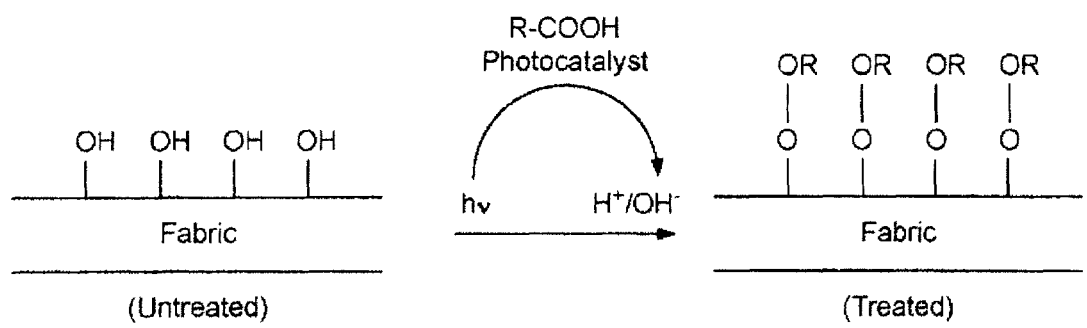
FIG. 4 is a schematic representation of one non-limiting embodiment of a mechanism of action of the compositions and methods described herein where a substrate surface is covalently modified.

FIG. 4 schematically illustrates one non-limiting embodiment of the compositions and methods described herein for treating substrates. A composition comprising an active material having a carboxyl group and a photocatalyst capable of generating an acid or a base upon exposure to light is provided in the presence of a substrate comprising surface hydroxyl groups. The photocatalyst is exposed to light, which causes the photocatalyst to form an acid or a base. The acid or base catalyzes the formation of a covalent ester bond between the hydroxyl group on the substrate and the carboxyl group on the active material.

Therefore, photocatalysis of the reactions forming ester and/or thioester covalent bonds between active components and substrates in the various embodiments of the compositions and methods described herein provides for an efficient, controllable, stable and physiologically acceptable approach to substrate treatment such as, for example, F-layer and stratum corneum repair and/or fortification in hair and skin respectively.

Figure 5:
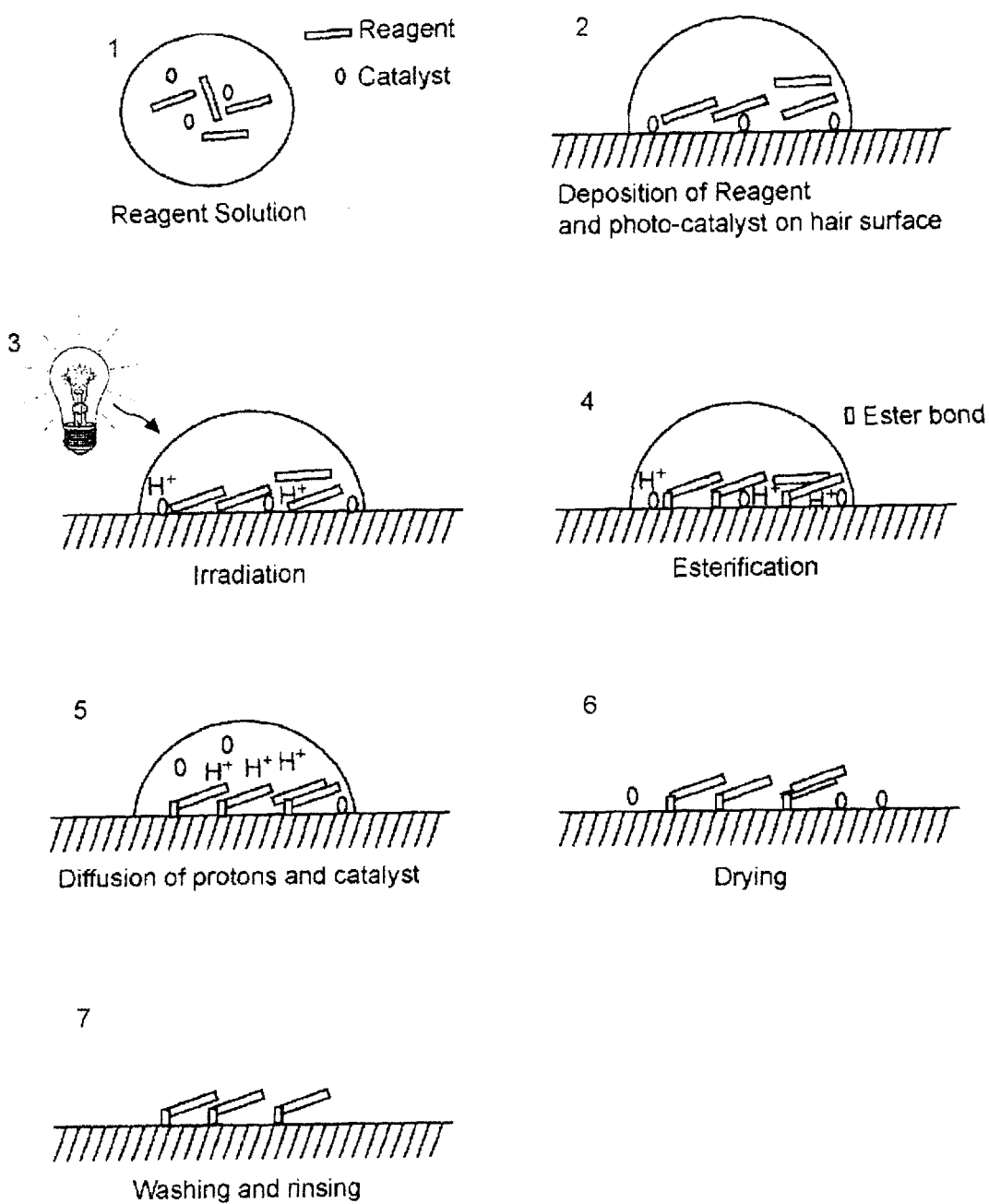
FIG. 5 is a schematic representation of non-limiting embodiment of a mechanism of action of the compositions and methods described herein where a substrate surface is covalently modified.

FIG. 5 is a schematic representation of one non-limiting embodiment of a mechanism of use of the compositions and methods described herein in the context of a photoacid catalyst. In the first step, a reagent solution is provided that includes a reagent, which may be an active component, and a photoacid catalyst. The reagent solution may comprise a shampoo, a conditioner, other personal care product or a consumer care product. In the second step, the reagent solution is applied to a substrate, which may be skin, hair, fabric, or a hard surface, for example. The components of the reagent solution deposit on the surface of the substrate. In the third step, the system comprising the reagent solution and the substrate is exposed to light. The light causes the deprotonation of the photocatalyst. In the fourth step, a photoacid-catalyzed esterification reaction occurs between the reagent and the substrate surface. In the fifth step, un-reacted catalyst, reagent, and protons diffuse from the substrate surface and are removed from the system. In the sixth step, the modified/functionalized substrate is dried. In the seventh step, the modified/functionalized substrate is washed and rinsed. The modified/functionalized substrate substantially retains the covalently bound reagent after washing and rinsing.

Figure 6:
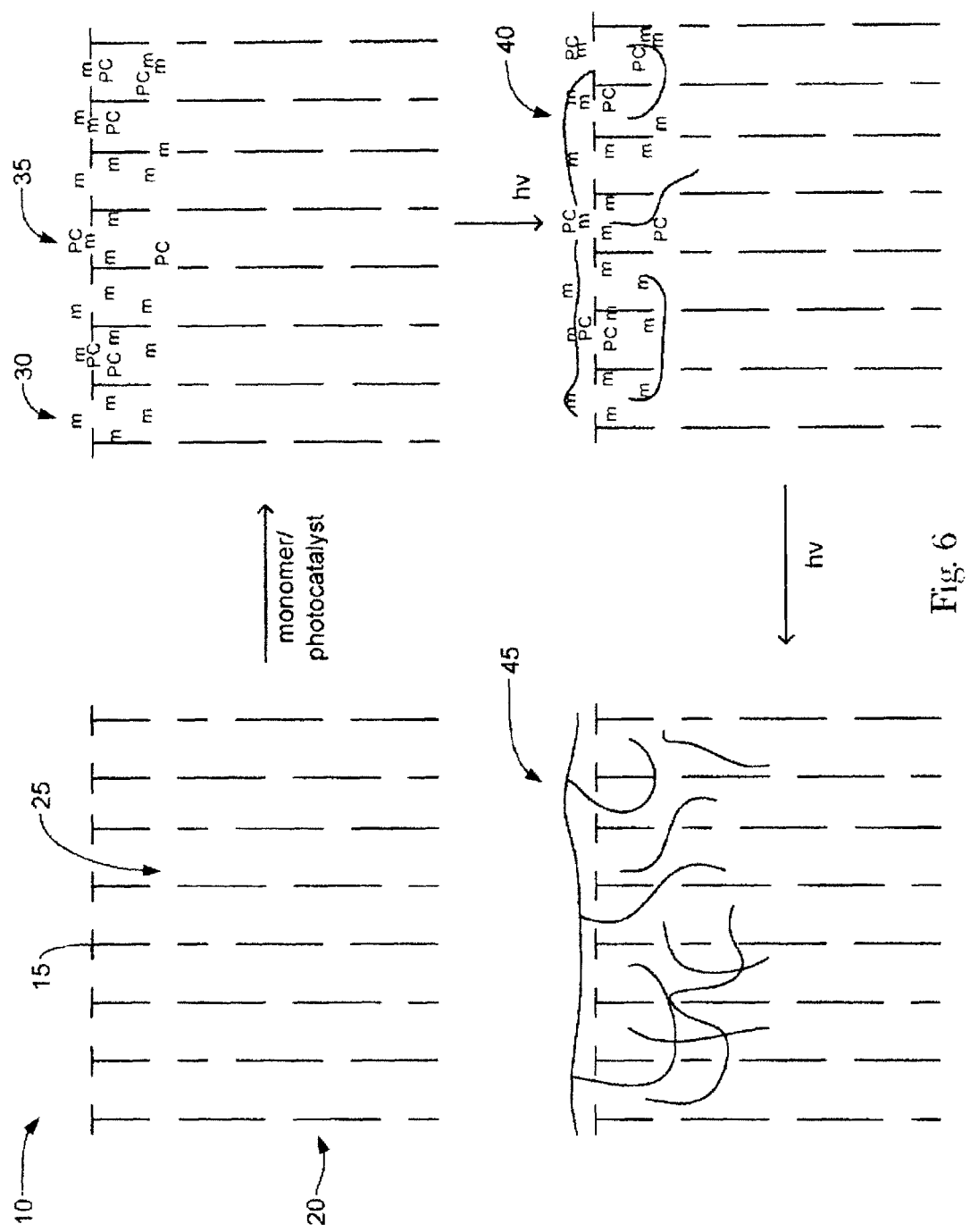
FIG. 6 is a schematic representation of non-limiting embodiment of a mechanism of action of the compositions and methods described herein where a porous substrate material is treated with an active material capable of forming a secondary active material.

FIG. 6 is a schematic representation of one non-limiting embodiment of the compositions and methods described herein. A porous substrate material 10 is provided. The substrate material 10 includes a substrate surface 15 and a bulk portion 20 having pores 25. The substrate material 10 is treated with a composition comprising an active material 30 and a photocatalyst 35. The active material 30 may comprise molecules capable of reacting together in the presence of an acid or a base to form a secondary compound. For example, the active material 30 may comprise one or more types of monomer capable of reacting to form polymer or copolymer in the presence of acid or base. The active material 30 and the photocatalyst 35 penetrate, at least in part, the surface 15 of the substrate 10 into the bulk portion 20 through pores 25. The substrate 10 is exposed to light of suitable wavelength to activate the photocatalyst 35, which generates acid or base to catalyze the reaction of the active material 30 on the surface 15 and/or in the bulk portion 20. At the time the active material is catalyzed and attaches the substrate, another active material, a secondary active material forms from two or more active components of the composition catalyzed in situ. This secondary active material 40 attaches to the surface 15 and/or in the bulk portion 20 of substrate material 10. Secondary active material 40 may comprise polymers, copolymers or combinations thereof, for example. The secondary active material 40 may form a polymer network 45 that may modify the surface and/or bulk properties of the substrate material 10.

The secondary active material formed according to the photocatalyzed acid or base mechanism described herein may localize to the surface and/or bulk of the substrate material. In various embodiments, the localization may be a result of covalent attachment of the secondary active material to the substrate material. In other embodiments, the localization may be a result of non-covalent chemical or physical interactions between the secondary active material and the surface and/or bulk of the substrate material. For example, FIG. 6 illustrates a secondary active material comprising a polymer network that is immobilized on the surface and partially in the bulk of a substrate material due to the physical formation of the polymer within pores located in the material. In other embodiments (not shown in FIG. 6), the secondary active material formed according to the photocatalyzed acid or base mechanism described herein may localize on the surface of a substrate and/or in the bulk of the substrate due to interactions such as adsorption, absorption, electrostatic interaction, frictional interaction steric interaction, and/or size exclusion effects. This allows for the manipulation of various material properties such as, for example, porosity of the treated substrate.

In various embodiments the active material and, or the secondary active material formed according to the photocatalyzed acid or base mechanism described herein may localize on the surface of a substrate and/or in the bulk of the substrate due to changes in the properties of the these material when covalent bonds form between their molecules. For example, where the active material comprises a monomer/polymer system, the active material may be polymerized and/or crosslinked on the surface of a substrate. The polymerization and/or crosslinking may change the solubility of the active material in the reaction medium, which may facilitate the deposition of the secondary active material onto the substrate surface. In this manner, a surface layer of secondary active material may form on the substrate surface thereby modifying the surface properties. This may result in the encapsulation of constituent fibers in fibrous substrates such as, for example, hair and fabrics. In various embodiments (not shown in FIG. 6) the photocatalyzation acid or base transforms the active material so it covalently bonds to the substrate (surface and/or bulk) as described herein.

The compositions and methods described herein facilitate in situ and localized modification of material properties in a controlled manner. The active components are covalently altered (e.g., by the formation of covalent bonds between them to form a secondary active material and/or between active components and a substrate material) in a photoacid or photobase reaction system.

The substrate to be modified may be treated by spraying, soaking, spreading, coating, rinsing, or any other suitable means of introducing the composition onto the surface of the substrate or into the bulk of the substrate material. In various embodiments, it is important to ensure the entire surface of the substrate is wetted by reagent solution in order to ensure sufficient modification of the substrate surface and/or bulk. If the active material is at least partially insoluble in the vehicle, it is important to maximize contact between the active material and the substrate by, for example, minimizing the drop size or particle size of the active in the vehicle. In various embodiments, it may be desired to introduce reagent solution onto only a single portion or multiple portions of a substrate surface. In other embodiments, it may be desired to irradiate only a single portion or multiple portions of a substrate surface with light of a wavelength suitable to activate the photocatalyst. The covalent modification only occurs on those areas of the substrate surface (and underlying bulk) that are both in contact with a reagent solution and irradiated with light of a wavelength suitable to activate the photocatalyst. This allows for control of the location and extent of the surface and/or bulk modification.

The acid or base photocatalytic covalent modification/functionalization mechanisms described herein may also be reversible. For example, substrate surfaces covalently modified or functionalized through esterification and/or thioesterification reactions may be contacted with an acidic aqueous surfactant solution. Alternatively, an alkaline surfactant solution may be employed. These solutions may facilitate the hydrolytic cleavage of the ester and/or thioester bonds attaching the active components to the substrate, thereby removing the active components.

This removability is limited to active component-substrate bonds that are reversible under the appropriate conditions. For example, in the case of photoacid-catalyzed esterification, the ester bond is formed when the reagent and the catalyst are present in the vicinity of the substrate and exposed to the appropriate light. The high concentration of protons at the moment of irradiation results in ester bond formation that remains intact because the generated protons diffuse rapidly into the bulk of the medium. The low content of the photoacid allows for subsequent stable and near-neutral pH of the bulk aqueous solution. Under these conditions the ester bond is hydrolyzed at a very slow rate. However, treatment with significantly lower (or significantly higher) pH aqueous solutions will more readily break the ester bonds resulting in the original unmodified substrate surface.

The removal of the covalently-attached active can also be achieved by treatment of the modified or functionalized substrate with a composition including a photocatalyst (photoacid or photobase). This allows for improved control over the timing of the removal of the active component from the substrate. This can be achieved if the photocatalyst is chosen so that it is unaffected by ambient light but can generate acid or base species under light of a specific wavelength provided by an appropriate device.

Each of the various components of the compositions and associated methods described herein, as well as preferred and optional components, are described in detail.

Active Material

The active material of the present invention comprises branched, cyclic, crosslinked and combinations of thereof silicone polymer, copolymer and combinations of polymers and copolymer having molecular weights of at least 150 grams/mole, alternatively 1000 grams/mole, from 3000 grams/mole to 10 million grams/mole, 10,000 grams/mole to 7 million grams/mole, or 50,000 grams/mole to 4 million grams/mole; and at least one organic functional group (and in one embodiment multiple groups), including but not limited to hydroxyl, amino, carboxyl sulphonate, thiol, epoxide, ester groups and/or any combination thereof, and iii) the level and nature of substitution and molecular weight of the silicone polymer or copolymer can be appropriately selected, depending on the desired substrate modification and application conditions. For example, if increased hydrophobicity is desired, less than 2% of the silicone atoms of the silicone polymer, copolymer and combination of polymer and copolymer can be substituted with organic groups. The silicone copolymer or copolymer can be from monomers which contain organic alcohol groups (primary and secondary) including those having the structure:

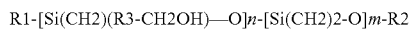

R1-[Si(CH2)(R3-CH2OH)—O]$n$-[Si(CH2)2-O]$m$-R2

Wherein R1, R2 methyl; R3-CH2CH2CH2-(OCH2CH2O)q-H with q≥1.

For example hair modification can be achieved by treating damaged hair with a silicone polymer and, or copolymer active material. Treatment with such an active material in emulsion, dispersion, and/or solutions with a photoacid generator, such as 8-hydroxyquinoline can provide damaged hair with benefits that are durable, for example, that are persistent after multiple shampoo wash cycles. Examples of durable benefits include hair softness (wet and dry), compatibility, anti-frizz, style and color retention, moisturization, and shine.

The surface modification method involves formation of covalent bonds between silicone polymer or copolymer and the substrate. The bonds are created by acid-catalyzed reaction of the primary or secondary alcohol of the polymer or copolymer with compatible functional groups of the hair substrate (for example carboxylic acid groups toward condensation).

Suitable silicone polymer and copolymers include those having an alkoxyalkanol group. In one embodiment the silicone polymer and, or copolymer is a Bis-Hydroxyethoxypropyl Dimethicone having the structure:

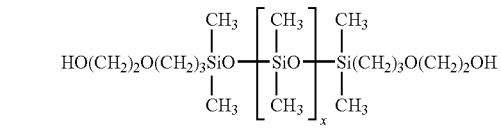

Suitable Bis-Hydroxyethoxypropyl Dimethicones include, but are not limited to, those materials available as 5562 Carbinol Fluid from Dow Corning, and Baysilone OF OH 702 E from Momentive.

Photocatalyst

The photocatalyst may be any acid, base (or conjugate thereof) having a pKa (or pKb) value that decreases (or increases) upon exposure to light. The light may be light of any suitable wavelength to result in the respective decrease or increase in pKa or pKb. For example the source of light may be ambient light, sunlight, incandescent light, fluorescent light, LED light, laser light, and the like. The light used in the present invention may The composition of the present invention utilize light within the electromagnetic spectrum ranging from infrared to visible and to ultraviolet light having wavelengths from about 1200 nm to about 200 nm. Using UV versus visible light (VIS) is not mutually exclusive as many photoactive materials have broad spectrum of absorption that covers both. Separately, in several instances it has been shown that chemical reactions activated by UV light can be measurable enhanced by VIS. In reality, one needs to consider the action spectrum of the entire reaction to define which wavelengths make important contributions to the outcome. It will be readily apparent to one of ordinary skill in the art that the appropriate wavelength or wavelengths of light will be dependant upon the identities of the one or more photocatalysts employed.

In addition, the suitable light may be provided from any source capable of illuminating the substrate surface. For example, ambient sunlight, incandescent light, fluorescent light, and the like may provide light of suitable wavelength. Accordingly, the light may be provided by conventional sources such as lamps and portable or battery-powered lights. In addition, specific devices may be developed or adapted for use with the compositions and method described herein. For example, a hair brush configured to incorporate LEDs that provide light of a suitable wavelength may be used to covalently modify the surface of fibers. In various embodiments, a laser may be used to provide precise targeting of the covalent modification of substrate surfaces, for example.

In various embodiments, the photocatalyst is a photoacid such as, for example, an aromatic hydroxy compound, a sulfonated pyrene compound, an onium salt, a diazomethane derivative, a bissulfone derivative, a disulfuno derivative, a nitrobenzyl sulfonate derivate, a sulfonic acid ester derivative, a sulfonic acid ester of an N-hydroxyimide, or combinations thereof.

Photoacid catalysts may include, for example, hydroxy-substituted aromatics such as, for example, 8-hydroxyquinoline, 8-hydroxyquinoline sulfate, 8-quinolinol-1-oxide, 5-hydroxyquinoline, 6-hydroxyquinoline, 7-hydroxyquinoline, 5-iodo-7-sulfo-8-hydroxyquinoline, 5-fluoro-8-hydroxyquinoline, 5-fluoro-7-chloro-8-hydroxyquinoline, 5-fluoro-7-bromo-8-hydroxyquinoline, 5-fluoro-7-iodo-8-hydroxyquinoline, 7-fluoro-8-hydroxyquinoline, 5-chloro-8-hydroxyquinoline, 5,7-dichloro-8-hydroxyquinoline, 5-chloro-7-bromo-8-hydroxyquinoline, 5-chloro-7-iodo-8-hydroxyquinoline, 7-chloro-8-hydroxyquinoline, 5-bromo-8-hydroxyquinoline, 5-bromo-7-chloro-8-hydroxyquinoline, 5,7-dibromo-8-hydroxyquinoline, 5-bromo-7-iodo-8-hydroxyquinoline, 7-bromo-8-hydroxyquinoline, 5-iodo-8-hydroxyquinoline, 5-iodo-7-chloro-8-hydroxyquinoline, 5,7-diiodo-8-hydroxyquinoline, 7-iodo-8-hydroxyquinoline, 5-sulfonic acid-8-hydroxyquinoline, 7-sulfonic acid-8-hydroxyquinoline, 5-sulfonic acid-7-iodo-8-hydroxyquinoline, 5-thiocyano-8-hydroxyquinoline, 5-chloro-8-hydroxyquinoline, 5-bromo-8-hydroxyquinoline, 5,7-dibromo-8-hydroxyquinoline, 5-iodo-8-hydroxyquinoline, 5,7-diiodo-8-hydroxyquinoline, 7-azaindole, 7-cyano-2-naphthol, 8-cyano-2-naphthol, 5-cyano-2-naphthol, 1-hydroxy-3,6,8-pyrenetrisulfonic acid, Trans-3-hydroxystilbene, 2-hydroxymethylphenol, or Pelargonidin.

Photoacid catalysts may include onium salts such as, for example, bis(4-tert-butylphenyl)iodonium perfluoro-1-butanesulfonate, diphenyliodonium perfluoro-1-butanesulfonate, diphenyliodonium-9,10-dimethoxyanthracene-2-sulfonate, diphenyliodonium hexafluorophosphate, diphenyliodonium nitrate, diphenyliodonium p-toluenesulfonate, diphenyliodonium triflate, (4-methylphenyl)diphenylsulfonium triflate, (4-methylthiophenyl)methyl phenyl sulfonium triflate, 2-naphthyl diphenylsulfonium triflate, (4-phenoxyphenyl)diphenylsulfonium triflate, (4-phenylthiophenyl)diphenylsulfonium triflate, thiobis(triphenyl sulfonium hexafluorophosphate), triarylsulfonium hexafluoroantimonate, triarylsulfonium hexafluorophosphate salt, triphenylsulfonium perfluoro-1-butanesulfonate, triphenylsulfonium triflate, tris(4-tert-butylphenyl)sulfonium perfluoro-1-butanesulfonate, tris(4-tert-butylphenyl)sulfonium triflate, bis(4-tert-butylphenyl)iodonium p-toluenesulfonate, bis(4-tert-butylphenyl)iodonium triflate, (4-bromophenyl)diphenylsulfonium triflate, (tert-butoxycarbonylmethoxynaphthyl)diphenylsulfonium triflate, (tert-butoxycarbonylmethoxyphenyl)diphenylsulfonium triflate, (4-tert-butylphenyl)diphenylsulfonium triflate, (4-chlorophenyl)diphenylsulfonium triflate, (4-fluorophenyl)diphenylsulfonium triflate, [4-[2-hydroxytetradecyl)oxy]phenyl]phenyliodonium hexafluoroantimonate, (4-iodophenyl)diphenylsulfonium triflate, (4-methoxyphenyl)diphenylsulfonium triflate, diphenyliodo hexafluorophosphate, diphenyliodo hexafluoroarsenate, diphenyliodo hexafluoroantimonate, diphenyl p-methoxyphenyl triflate, diphenyl p-toluenyl triflate, diphenyl p-isobutylphenyl triflate, diphenyl p-t-butylphenyl triflate, triphenylsulfonium hexafluoroarsenate, triphenylsulfonium hexafluorophosphate, triphenylsulfonium hexafluoroantimonate, triphenylsulfonium triflate, dibutylnaphthyl sulfonium triflate, diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)-sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethyl-sulfonium trifluoromethanesulfonate, trimethylsulfonium p-toluenesulfonate, cyclohexylmethyl(2-oxocyclohexyl)-sulfonium trifluoromethanesulfonate, cyclohexylmethyl(2oxocyclohexyl) sulfonium p-toluenesulfonate, dimethylphenyl-sulfonium trifluoromethanesulfonate, dimethylphenyl-sulfonium p-toluenesulfonate, dicyclohexylphenylsulfonium trifluoromethanesulfonate, dicyclohexylphenylsulfonium p-toluenesulfonate, trinaphthylsulfonium trifluoromethane-sulfonate, cyclohexylmethyl(2-oxocyclohexyl)sulfonium trifluoromethanesulfonate, (2-norbornyl)methyl(2-oxocyclo-hexyl)sulfonium trifluoromethanesulfonate, ethylenebis[methyl(2-oxocyclopentyl)sulfonium trifluoromethane-sulfonate], or 1,2'-naphthylcarbonylmethyltetrahydrothiophenium triflate.

Photoacid catalysts may include diazomethane derivatives such as, for example, bis(benzenesulfonyl)-diazomethane, bis(p-toluenesulfonyl)diazomethane, bis(xylenesulfonyl)diazomethane, bis(cyclohexylsulfonyl)-diazomethane, bis(cyclopentylsulfonyl)diazomethane, bis(n-butylsulfonyl)diazomethane, bis(isobutylsulfonyl)-diazomethane, bis(sec-butylsulfonyl)diazomethane, bis(n-propylsulfonyl)diazomethane, bis(isopropylsulfonyl)-diazomethane, bis(tert-butylsulfonyl)diazomethane, bis(n-amylsulfonyl)diazomethane, bis(isoamylsulfonyl)-diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, or 1-tert-amylsulfonyl-1-(tert-butylsulfonyl)diazomethane.

Photoacid catalysts may include glyoxime derivatives such as, for example, bis-o-(p-toluene-sulfonyl)-α-dimethylglyoxime, bis-o-(p-toluenesulfonyl)-α-diphenylglyoxime, bis-o-(p-toluenesulfonyl)-α-dicyclohexyl-glyoxime, bis-o-(p-toluenesulfonyl)-2,3-pentanedioneglyoxime, bis-o-(p-toluenesulfonyl)-2-methyl-3,4-pentane-dioneglyoxime, bis-o-(n-butanesulfonyl)-α-dimethylglyoxime, bis-o-(n-butanesulfonyl)-α-diphenylglyoxime, bis-o-(n-butanesulfonyl)-α-dicyclohexylglyoxime, bis-o-(n-butanesulfonyl)-2,3-pentanedioneglyoxime, bis-o-(n-butanesulfonyl)-2-methyl-3,4-pentanedioneglyoxime, bis-o-(methanesulfonyl)-α-dimethylglyoxime, bis-o-(trifluoromethanesulfonyl)-α-dimethylglyoxime, bis-o-(1,1,1-trifluoroethanesulfonyl)-α-dimethylglyoxime, bis-o-(tert-butanesulfonyl)-α-dimethylglyoxime, bis-o-(perfluorooctanesulfonyl)-α-dimethylglyoxime, bis-o-(cyclohexane-sulfonyl)-α-dimethylglyoxime, bis-o-(benzenesulfonyl)-α-dimethylglyoxime, bis-o-(p-fluorobenzenesulfonyl)-α-dimethylglyoxime, bis-o-(p-tert-butylbenzenesulfonyl)-α-dimethylglyoxime, bis-o-(xylenesulfonyl)-α-dimethyl-glyoxime, or bis-o-(camphorsulfonyl)-α-dimethylglyoxime.

Photoacid catalysts may include bissulfone derivatives such as, for example, bisnaphthylsulfonylmethane, bistrifluoromethylsulfonylmethane, Bismethylsulfonylmethane, bisethylsulfonylmethane, bispropylsulfonylmethane, bisisopropylsulfonylmethane, bis-p-toluenesulfonylmethane, bisbenzenesulfonylmethane, 2-cyclohexyl-carbonyl-2-(p-toluenesulfonyl)propane (β-ketosulfone derivative), 2-isopropylcarbonyl-2-(p-toluenesulfonyl) propane (β-ketosulfone derivative).

Photoacid catalysts may include disulfono derivatives such as, for example, diphenyl disulfone or dicyclohexyl disulfone.

Photoacid catalysts may include nitrobenzyl sulfonate derivatives such as, for example, 2,6-dinitrobenzyl p-toluenesulfonate or 2,4-dinitrobenzyl p-toluenesulfonate.

Photoacid catalysts may include sulfonic acid ester derivatives such as, for example, 1,2,3-tris(methanesulfonyloxy)benzene, 1,2,3-tris(trifluoro-methanesulfonyloxy)benzene, or 1,2,3-tris(p-toluenesulfonyloxy)benzene.

Photoacid catalysts may include sulfonic acid esters of N-hydroxyimides such as, for example, N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethyl-benzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethane-sulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzenesulfonate, N-hydroxyphthalimide trifluoromethanesulfonate, N-hydroxyphthalimide p-toluenesulfonate, N-hydroxynaphthalimide methanesulfonate, N-hydroxynaphthalimide benzenesulfonate, N-hydroxy-5-norbornene-2,3-dicarboxylmide methanesulfonate, N-hydroxy-5-norbornene-2,3-dicarboxylmide trifluoromethanesulfonate, N-hydroxy-5-norbornene-2,3-dicarboxylmide p-toluenesulfonate, N-hydroxynaphthalimide triflate, N-hydroxy-5-norbornene-2,3-dicarboximide perfluoro-1-butanesulfonate.

In certain embodiments, the photocatalyst is 8-hydroxyquinoline, which may act as a photoacid catalyst in lower pH solutions or as a photobase catalyst in higher pH solutions. In certain other embodiments, the photocatalyst is 8-hydroxy-1,3,6-pyrenetrisulfonic acid trisodium salt (D&C Green 8). In various embodiments, the photocatalyst is a photobase. Photobase catalysts may include derivatives of trityl alcohols such as, for example, Malachite green. Photobase catalysts may also include acridine derivatives such as, for example, 9-hydroxy-10-methyl-9-phenyl-9,10-dihydroacridine. Photobase catalysts may also include photoactive carbamate-containing compounds.

The photocatalyst may be present in the compositions and methods described herein in an amount from 0.00050 percent to 30 percent by weight relative to the total weight of the composition. Generally, there is a preferred concentration of the photocatalyst. The preferred concentration of photocatalyst depends, in part, on a variety of factors including, for example, the chemical structure of the catalyst, the reaction medium, the reaction type, and the substrate.

Vehicle

The compositions described herein generally include a vehicle suitable for dispersing or dissolving the active material, the photocatalyst, and any other components to facilitate application of the active material onto the substrate surface or into the bulk portions of the substrate. The vehicle may comprise one or more of a solvent, an emulsifier, a surfactant, or other dispersant. The properties of a suitable vehicle are dependant, at least in part, on the properties of the other components of the composition and the substrate to be modified. For example, when using in a composition intended to be applied to physiological tissues, the vehicle for that composition is selected so as not to destabilize the composition as well as avoid creating problems such as irritation or insult to the targeted physiologically tissue as well as the non-targeted surrounding tissues.

A suitable vehicle operates to disperse or dissolve the active material, the photocatalyst, and any other components, and to facilitate application of the active material onto the substrate surface. A suitable vehicle facilitates sufficient contact between the active material and the substrate. In one embodiment, a physiologically acceptable vehicle may be any carrier, solvent, or solvent-containing composition that is suitable for application to physiological tissues such as human hair and human skin.

As previously stated, a suitable vehicle may be a solvent. For example, water is generally considered a useful solvent in consumer care products including personal care products. In various consumer care products including those of the present invention, water may be used in levels from 1% to 98% by weight of the composition. Water is particularly useful in personal care products as it does not insult physiologically tissues. Additional solvent or solvent-containing vehicles include, but are not limited to, hydroxyl-containing liquids (e.g., alcohols), silicones, oils, hydrocarbons, glycols, ammonium lauryl sulfate, sodium lauryl sulfate, and combinations thereof. In certain embodiments, for example, where the active material is at least partially insoluble in water, other solvents, dispersants, or emulsifiers may be used as acceptable vehicles, alone or in combination with each other and/or with water.

A suitable vehicle is therefore generally used to dilute and/or emulsify the components forming the compositions described herein. A suitable vehicle may dissolve a component (true solution or micellar solution) or a component may be dispersed throughout the vehicle (suspension, dispersion or emulsion). The vehicle of suspension, dispersion or emulsion is typically the continuous phase thereof. That is, other components of the suspension, dispersion or emulsion are distributed on a molecular level or as discrete or agglomerated particles throughout the vehicle. The preparation of such emulsions or dispersions of the active in these cases may be highly important. Small particles contribute to an intimate contact between the active, the substrate and the photoacid catalyst, increasing the reaction rate. For example, in the case of a fibrous surface modification using fatty alcohol and 8-hydroxyquinoline in a water medium, an emulsion that contains very small particles (for example, less than 500 nanometers or more preferably less than 200 nanometers) may be substantially more effective in providing a durable hydrophobic surface than an emulsion containing larger particles It will be readily apparent to one of ordinary skill in the art that the appropriate vehicle(s) are dependent upon the specific active material(s), photocatalyst(s), and other optional component(s) used in the compositions described herein.

Optional Components

The compositions and methods described herein may optionally include a variety of components. For example, in various embodiments, the compositions and methods described herein may include surfactants, emulsifiers, oxidants, reductants, pH regulators, emollients, humectants, proteins, peptides, amino acids, additive polymer or copolymers, glossers, oils and/or fatty acids, lubricants, sequestrants/chelators, antistatic agents, rheology modifiers, feel agents, fillers, dyes, pigments preservatives, perfumes, medicaments other functional components, or combinations thereof. Particular optional components may be found in the CTFA International Cosmetic Ingredient Dictionary, Tenth Edition, 2004; and in McCutcheon, Detergents and Emulsifiers, North American Edition (1986). It will be readily apparent to one of ordinary skill in the art that the particular optional components utilized will be dependant, at least in part, upon the specific applications for the compositions and methods.

In various embodiments, the compositions and methods described herein include an oxidizing agent (oxidant). An oxidant may be added, for example, to render a substrate surface more amenable to photocatalytic covalent modification/functionalization in accordance with the various embodiments described herein. An oxidant may be present in an amount form 0.00050% to 25% 0.1% to 10% 0.5% to 5% by weight relative to the total weight of the composition. Suitable oxidants include, for example, one or more of hydrogen peroxide, urea peroxide, melamine peroxide, percarbonates, peracids, alkali metal bromates, perborates, bromates, hypochlorites, chlorites, perchlorates, iodates, periodates, permanganates and persulfates. In certain embodiments, the oxidant is hydrogen peroxide.

The identity of the reaction system, the quantities and concentrations of reagents utilized, and the reaction conditions are all dependent, at least in part, upon the substrate to be modified, the active material utilized, and the manner in which the active material is to be associated with the substrate. These considerations are readily determinable by one of ordinary skill in the art in practice of the compositions and methods described herein.

EXAMPLES

The following examples are intended to more clearly illustrate aspects of the compositions and methods described herein, but are not intended to limit the scope thereof.

Example 1A

Preparation of Prototype Silicone Emulsion 1A

Add 200 mL of tetrahydrofuran into a 500-mL beaker. Then add 6.0 grams of silicone polymer or copolymer (Dow Corning® 5562 Carbinol Fluid). Dissolve the solution with mild mixing. Add 200 mL of water in a dropwise fashion taking about 15 minutes or longer under high shear using a Silverson® L4RT homogenizer at 6000 rpm. Continually mix the resulting emulsion under high shear for 2 more hours. Add 0.030 grams of 8-hydroxyquinoline and stir for 10 minutes.

Example 1B

Preparation of Prototype Silicone Emulsion 1B

Repeat the procedure of Example 1A, but replace the Dow Corning® 5562 Fluid with Momentive® Silicone Polymer, Baysilone OF OH 702E

Example 2A

Hair Treatment by Dipping in Prototype Silicone Emulsion 1A

Bleach a 20 cm long (4.0-gram) hair switch and wash and air dry. In a dark room, dip the hair switch into a beaker containing 100.0 g of the emulsion from Example 1A. Remove the hair switch from the beaker after 15 minutes and expose to a bright light (Aquarium 20W Fluorescent tube AquaRays® Model No F20WT12-AR-FS) for 15 minute. Rinse the hair switch with a 100 mL of methyl isobutyl ketone/toluene (1:1) 3 times and then dip it into a fresh solution of 250 mL of this solvent mixture for 30 minutes. Hang switch to air dry. Upon drying, wash the switch with clarifying shampoo (Pantene Pro-V® Clarifying Shampoo), thoroughly rinse with running tap water for 3.0 minutes, and air dry for at least 5 hours. Repeat the washing/rinsing cycle 3 times. Perform this procedure with two more identical hair switches (from the same lot or source).

Example 2B

Hair Treatment by Dipping in Prototype Silicone Emulsion 1B

Repeat the procedure of Example 2A, replacing Prototype Silicone Emulsion 1A with Prototype Silicone Emulsion 1B.

Example 3

Fabric Treatment by Dipping in Prototype Silicone Emulsion 1A

Wash and air dry a 20 cm long (4.0-gram) piece of cotton fabric. In a dark room, dip the fabric switch into a beaker containing 100.0 g of the emulsion from Example 1A. Remove the fabric from the beaker after 15 minutes and expose it to a bright light (Aquarium 20W Fluorescent tube AquaRays® Model No F20WT12-AR-FS) for 15 minute. Rinse the fabric with a 100 mL of methyl isobutyl ketone/toluene (1:1) 3 times and then dip into a fresh solution of 250 mL of this solvent mixture for 30 minutes. Hand and air dry the fabric and wash it using Tide® liquid detergent at the dilution concentration found on the product label. Thoroughly rinse and air dry the fabric for at least 5 hours. Repeat the washing/rinsing cycle 3 times. Repeat the procedure with two more identical fabrics (from the same lot).

Example 4

Fabric Treatment by Spraying with Prototype Silicone Emulsion 1A

Wash and air dry a 20 cm long (4.0-gram) piece of cotton fabric. In a dark room, spray the fabric switch with 10.0 g of the emulsion from Example 1A. Expose the fabric is to bright light (Aquarium 20W Fluorescent tube AquaRays® Model No F20WT12-AR-FS) for 15 minute. Rinse the fabric with a 100 mL of methyl isobutyl ketone/toluene (1:1) 3 times and then dip into a fresh solution of 250 mL of this solvent mixture for 30 minutes. Hang to air dry and upon completely drying, wash with Tide® liquid detergent at the dilution concentration found on the product label. Thoroughly rinse, and air dry for at least 5 hours. Repeat the washing and rinsing cycle three times. The procedure is repeated with two more identical fabrics (from the same lot).

Example 5

Fabric Treatment by Adding Prototype Silicone Emulsion 1A to a Laundry Detergent Wash and air dry five 10 cm×10 cm pieces of cotton fabric. In a dark room, add the fabric to 10 L of a Tide® liquid detergent wash solution at the dilution concentration found on the product label and 100.0 g of the emulsion of Example 1A. Wash the fabric with agitation for about 15 minutes. Remove the fabric from the wash solution and expose to a bright light (Aquarium 20W Fluorescent tube AquaRays® Model No F20WT12-AR-FS) for 15 minute. Rinse the fabric with a 100 mL of methyl isobutyl ketone/toluene (1:1) 3 times and then dip into a fresh solution of 250 mL of this solvent mixture for 30 minutes. Hang the fabric to air dry. After drying, wash the fabric with Tide® liquid detergent at the dilution concentration found on the product label, thoroughly rinse and air dried for at least 5 hours. The washing/rinsing is repeated 3 times.

Example 6

Fabric Treatment by Adding Prototype Silicone Emulsion 1B to a Laundry Detergent Wash and air dry five 10 cm×10 cm pieces of cotton fabric. In a dark room, add the fabric is added to 10 L of a Tide® liquid detergent at the dilution concentration found on the product label and 100.0 g of the emulsion from Example 1B. Wash the fabric with agitation for 15 minutes, removing the fabric and exposing to a bright light (Aquarium 20W Fluorescent tube AquaRays® Model No F20WT12-AR-FS) for 15 minute. Rinse the fabric with a 100 mL of methyl isobutyl ketone/toluene (1:1) 3 times and then dip into a fresh solution of 250 mL of this solvent mixture for 30 minutes. Hang to air dry and upon drying, wash the fabric with Tide® liquid detergent at the dilution concentration found on the product label and thoroughly rinse. Air dry for at least 5 hours. Repeat the washing/rinsing cycle 3 times

Example 7

Hard Surface Treatment by Spraying with Prototype Silicone Emulsion 1A

Wash and air dry a 10 cm×10 cm long white ceramic tile. In a dark room, spray the tile with 10.0 g of the emulsion from Example 1A. Expose the tile to a bright light (Aquarium 20 W Fluorescent tube AquaRays® Model No F20WT12-AR-FS) for 15 minute. Rinse the tile with a 100 mL of methyl isobutyl ketone/toluene (1:1) 3 times and then dip into a fresh solution of 250 mL of this solvent mixture for 30 minutes. Hang to air dry where upon drying, wash it with Mr Clean® cleaner, thoroughly rinse, and air dry for at least 5 hours. Repeat the washing and rinsing cycle 3 times. Repeat the procedure on a 10 cm×10 cm piece of glass and a 10 cm×10 cm piece of painted metal (car panel).

Example 8

Fabric Treatment by Spraying with Prototype Silicone Emulsion 1C

Wash and air dry a 20 cm long (4.0-gram) piece of cotton fabric. In a dark room, spray the fabric switch with 10.0 g of the emulsion from Example 1C. Expose the fabric to a bright light (Aquarium 20 W Fluorescent tube AquaRays® Model No F20WT12-AR-FS) for 15 minute. Rinse the fabric with a 100 mL of methyl isobutyl ketone/toluene (1:1) 3 times and then dip into a fresh solution of 250 mL of this solvent mixture for 30 minutes, and allow to air dry. Upon drying wash with Tide® liquid detergent at the dilution concentration found on the product label, thoroughly rinse and air dry for at least 5 hours. Repeat the washing/rinsing cycle 3 times. Repeat the procedure with two more identical fabrics (from the same lot).

Example 9

Fabric Treatment by Dipping in Prototype Silicone Emulsion 1D

Wash and air dry a 20 cm long (4.0-gram) piece of cotton fabric. In a dark room, dip the fabric switch into a beaker containing 100.0 g of the emulsion from Example 1D. Remove the fabric from the beaker after 15 minutes and expose to a bright light (Aquarium 20 W Fluorescent tube AquaRays® Model No F20WT12-AR-FS) for 15 minute. Rinse the fabric with a 100 mL of a one to one ratio by volume methyl isobutyl ketone to toluene 3 times and then dip into a fresh solution of 250 mL of this solvent mixture for 30 minutes, and hang to air dry. After drying, wash with Tide® liquid detergent at the dilution concentration found on the product label, thoroughly rinse and air dry for at least 5 hours. Repeat the washing/rinsing cycle 3 times. Repeat the procedure with two more identical fabrics (from the same lot).

Example 10

Fabric Treatment by Dipping in Prototype Silicone Emulsion 1F

Wash and air dry a 20 cm long (4.0-gram) piece of cotton fabric. In a dark room dip the fabric switch into a beaker containing 100.0 g of the emulsion from Example 1F. Remove the fabric removed from the beaker after 15 minutes and expose to a bright light (Aquarium 20 W Fluorescent tube AquaRays® Model No F20WT12-AR-FS) for 15 minute. Rinse the fabric with a 100 mL of one to one by volume ratio of methyl isobutyl ketone/toluene 3 times and then dip into a fresh solution of 250 mL of this solvent mixture for 30 minutes, and hang dry. After drying, wash with Tide® liquid detergent at the dilution concentration found on the product label and thoroughly rinse. Air dry for at least 5 hours. Repeat the washing/rinsing cycle 3 times. Repeat the procedure with two more identical fabrics (from the same lot).

Example 11

Hard Surface Treatment by Spraying with Prototype Silicone Emulsion 1E

Wash and air dry a 10 cm×10 cm long white ceramic tile. In a dark room, spray the tile with 10.0 g of the emulsion from Example 1E. Expose the tile to a bright light (Aquarium 20 W Fluorescent tube AquaRays® Model No F20WT12-AR-FS) for 15 minute. Rinse the tile with a 100 mL of one to one volume ratio of methyl isobutyl ketone/toluene 3 times and then dip into a fresh solution of 250 mL of this solvent mixture for 30 minutes, and air dry. Upon drying, wash with Mr Clean® cleaner, thoroughly rinse, and air dry for at least 5 hours. Repeat the washing/rinsing cycle 3 times. Repeat the procedure on a 10 cm×10 cm piece of glass and a 10 cm×10 cm piece of painted metal such as an automobile side panel.

Example 12

Hard Surface Treatment by Spraying with Prototype Silicone Emulsion 1D

Wash and air dry a 10 cm×10 cm long white ceramic tile. In a dark room, spray the tile with 10.0 g of the emulsion from Example 1D. Expose the tile to a bright light (Aquarium 20 W Fluorescent tube AquaRays® Model No F20WT12-AR-FS) for 15 minute. Rinse the tile with a 100 mL of one to one volume ratio of methyl isobutyl ketone/toluene 3 time. Dip the tile into a fresh solution of 250 mL of this solvent mixture for 30 minutes, air dry. Upon drying, wash with Mr Clean® cleaner, thoroughly rinse and air dry for at least 5 hours. Repeat the washing/rinsing cycle 3 times. Repeat the procedure on a 10 cm×10 cm piece of glass and a 10 cm×10 cm piece of painted metal such as an automobile side panel.

Example 13

Fabric Treatment by Adding Prototype Silicone Emulsion 1D to a Laundry Detergent Wash and air dry five 10 cm×10 cm pieces of cotton fabric. In a dark room, add the fabric to 10 L of a Tide® liquid detergent wash solution at the dilution concentration found on the product label and 100.0 g of the emulsion from Example 1D. Wash the fabric with agitation for 15 minutes. Remove the fabric from the wash solution and expose to a bright light (Aquarium 20 W Fluorescent tube AquaRays® Model No F20WT12-AR-FS) for 15 minute. Rinse the fabric with a 100 mL of a one to one ratio by volume of methyl isobutyl ketone/toluene 3 times and dip into a fresh solution of 250 mL of this solvent mixture for 30 minutes. Hang dry. Upon drying, wash with Tide® liquid detergent at the dilution concentration found on the product label, thoroughly rinse and air dry for at least 5 hours. Repeat the washing/rinsing cycle 3 times

Example 14

Hard Surface Treatment by Spraying with Prototype Silicone Emulsion 1C

Wash and air dry a 10 cm×10 cm long white ceramic tile. In a dark room, spray the tile with 10.0 g of the emulsion from Example 1C. Expose the tile to a bright light (Aquarium 20 W Fluorescent tube AquaRays® Model No F20WT12-AR-FS) for 15 minute. Rinse the tile with a 100 mL of a one to one ratio by volume methyl isobutyl ketone/toluene 3 times and dip into a fresh solution of 250 mL of this solvent mixture for 30 minutes. Air dry. Upon drying, wash tile with Mr. Clean® cleaner, thoroughly rinse and air dry for at least 5 hours. Repeat the washing/rinsing cycle 3 times. Repeat the procedure on a 10 cm×10 cm piece of glass and a 10 cm×10 cm piece of painted metal such as an automobile side panel.

The various embodiments of the compositions and methods described herein are primarily discussed in connection with hair, skin and fabric substrates. Nevertheless, it is recognized that the invention set forth in the following claims is not limited in application to any particular substrate. The invention set forth in the following claims may be used in connection with any substrate for which it is useful to treat the surface with the compositions and methods described herein as recognizable by one of ordinary skill in the art. Non-limiting examples of such substrates include, for example, fabric, paper, wood, plastic, glass, tile, stone, concrete, brick, other ceramics, and composites.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer care composition for treating a substrate comprising:
   (a) an active material that in the presence of an acid or a base has one or more functional groups forming covalent attachments to the substrate's complementary functional groups;
   (b) a photocatalyst capable of generating an acid or a base upon exposure to light, wherein the photocatalyst absorbs light within electromagnetic spectrum from infrared to visible and to ultraviolet light, from 1200 nm to 200 nm, and wherein the photocatalyst is a photoacid selected from the group consisting of aromatic hydroxyl compounds, sulfonated pyrene compounds, onium salts, diazomethane derivatives, bissulfone derivatives, disulfuno derivatives, nitrobenzyl sulfonate derivatives, sulfonic acid ester derivatives, sulfonic acid esters of N-hydroxyimides, and combinations thereof; and
   (c) a delivery vehicle for the combination of elements 1(a) and 1(b);
   wherein the substrate excludes physiological materials.

2. The composition recited in claim 1 wherein the delivery vehicle is a solvent capable of dissolving and dispersing the active material.

3. The composition recited in claim 2 wherein the delivery vehicle is selected from the group consisting of water, silicones, oils, hydrocarbons, lauryl sulfate salts and combinations thereof.

4. The composition recited in claim 1 wherein the photoacid is an aromatic hydroxyl compound.

5. The composition recited in claim 1 wherein the active material is selected from the group of hydrophilic active materials, hydrophobic active materials and mixtures thereof.

6. The composition recited in claim 5 wherein the active material is a hydrophobic material.

7. The composition recited in claim 6 wherein the hydrophobic active material is selected from the group consisting of a fatty acid, a fatty alcohol, a fatty amine, an aminosilicone, a polyvinyl alcohol, a polyvinyl alcohol-polyvinyl pyrrolidone copolymer, a polycaprolactone, an optical brightener, a humectant, a silanol, a dimethylsilicone functionalized with one or more of primary, secondary, carboxyl or hydroxyl functional groups, and combinations thereof.

8. The composition recited in claim 7 further comprising a surfactant, an emulsifier, an adjunct selected from the group consisting of an oxidant, a pH controlling component, a feel agent, a rheology modifier, a filler, a perfume, and combinations thereof.

9. The composition recited in claim 1 wherein the substrate is selected from the group consisting of fabric, paper, wood, plastic, glass, tile, stone, concrete, brick, other ceramics, glass, metal, polymeric films, composites, laminates, painted and varnished surfaces of the above and all combinations thereof.

10. The composition recited in claim 9 wherein the composition is selected from the group consisting of a soft surface cleaner, a hard surface cleaner, a glass cleaner, a ceramic tile cleaner, a toilet bowl cleaner, a wood cleaner, a multi-surface cleaner, a surface disinfectant, a dishwashing composition, a laundry detergent, a fabric conditioner, a fabric dye, a motor vehicle surface treatment, a surface protectant, and a surface disinfectant.

11. The composition recited in claim 10 wherein the photocatalyst is present in an amount from 0.00050% to 10% by weight relative to the total weight of the composition.

12. The composition recited in claim 9 wherein water is present in an amount from 1% to 98% by weight relative to the total weight of the composition.

13. The composition recited in claim 12 further comprising an oxidant present in an amount from 0.00050% to 25% by weight relative to the total weight of the composition.

14. The composition recited in claim 13 wherein the oxidant is hydrogen peroxide.

15. A method for treating a substrate with the composition of claim 1 wherein the method comprising the following steps:
   a) applying at least one photocatalyst to the substrate; and
   b) exposing the photocatalyst and the at least one active material to light for forming covalent attachments between one or more of the functional groups attached to the active material and the substrate;
   wherein the substrate excludes physiological materials.

* * * * *